US012599358B2

(12) United States Patent
Cormier et al.

(10) Patent No.: US 12,599,358 B2
(45) Date of Patent: Apr. 14, 2026

(54) METHODS AND SYSTEMS FOR ULTRASOUND IMAGING OF A BODY IN MOTION

(71) Applicant: POLYVALOR, LIMITED PARTNERSHIP, Montréal (CA)

(72) Inventors: Philippe Cormier, Longueuil (CA); Jonathan Poree, Montréal (CA); Jean Provost, Montréal (CA)

(73) Assignee: POLYVALOR, LIMITED PARTNERSHIP

( * ) Notice: Subject to any disclaimer, the term of this patent is extended or adjusted under 35 U.S.C. 154(b) by 311 days.

(21) Appl. No.: 18/019,650

(22) PCT Filed: Aug. 5, 2021

(86) PCT No.: PCT/CA2021/051088
§ 371 (c)(1),
(2) Date: Feb. 3, 2023

(87) PCT Pub. No.: WO2022/027135
PCT Pub. Date: Feb. 10, 2022

(65) Prior Publication Data
US 2023/0301623 A1 Sep. 28, 2023

Related U.S. Application Data

(60) Provisional application No. 63/061,925, filed on Aug. 6, 2020.

(51) Int. Cl.
*A61B 8/00* (2006.01)
*A61B 8/08* (2006.01)

(52) U.S. Cl.
CPC ............ *A61B 8/0883* (2013.01); *A61B 8/481* (2013.01); *A61B 8/488* (2013.01); *A61B 8/543* (2013.01)

(58) Field of Classification Search
CPC ................................ A61B 8/488; A61B 8/481
See application file for complete search history.

(56) References Cited

U.S. PATENT DOCUMENTS

2007/0282202 A1 12/2007 Maurice et al.
2020/0187910 A1* 6/2020 Pinton .................... A61B 8/481

OTHER PUBLICATIONS

Robert M Pohlman, Tomy Varghese, Physiological Motion Reduction using Lagrangian Tracking for Electrode Displacement Elastography, 2019 (Year: 2019).*

(Continued)

*Primary Examiner* — Pascal M Bui Pho
*Assistant Examiner* — Gabriel Victor Popescu
(74) *Attorney, Agent, or Firm* — NORTON ROSE FULBRIGHT CANADA LLP

(57) ABSTRACT

There is provided a method and a system for ultrasound imaging in presence of relative motion between a body and an imaging probe. A plurality of Eulerian-based ultrasound images of the body acquired at successive times T with the imaging probe is obtained. Lagrangian coordinates for the body are computed using data from the Eulerian-based ultrasound images. Lagrangian-based ultrasound images of the body are formed by providing the data from the Eulerian-based ultrasound images in the Lagrangian coordinate system.

20 Claims, 13 Drawing Sheets

(56)                    References Cited

OTHER PUBLICATIONS

G.B. J. Mancini, G. Gosselin, B. Chow, W. Kostuk, J., Stone, K. J. Yvorchuk, B. L. Abramson, R. Cartier, V. Huckell, J-C. Tardif, K. Connelly, J. Ducas, M. E. Farkouh, M. Gupta, M. Juneau, B. O'Neill, P. Raggi, K. Teo, S. Verma, R. Zimmermann, "Canadian Cardiovascular Society Guidelines for the Diagnosis and Management of Stable Ischemic Heart Disease," Canadian Journal of Cardiology, vol. 30, No. 8, pp. 837-849, Aug. 2014, doi: 10.1016/j.cjca.2014.05.013.

P. A. L. Tonino, W. F. Fearon, B. De Bruyne, K. G. Oldroyd, M. A. Leesar, p. N. Ver Lee, Md, p. A. Maccarthy, M. Van't Veer, N. H. J. Pijls, "Angiographic Versus Functional Severity of Coronary Artery Stenoses in the FAME Study," Journal of the American College of Cardiology, vol. 55, No. 25, pp. 2816-2821, Jun. 2010, doi: 10.1016/j.jacc.2009.11.096.

D. Garcia, B. Harbaoui, T. P. Van De Hoef, M. Meuwissen, S. S. Nijjer, M. Echavarria-Pinto, J. E. Davies, J. J. Piek, P. Lantelme, "Relationship between FFR, CFR and coronary microvascular resistance—Practical implications for FFR-guided percutaneous coronary intervention," PLoS ONE, vol. 14, No. 1, p. e0208612, Jan. 2019, doi: 10.1371/journal.pone.0208612.

P. G. Camici, G. D'Aamati, O. Rimoldi, "Coronary microvascular dysfunction: mechanisms and functional assessment," Nat Rev Cardiol, vol. 12, No. 1, pp. 48-62, Jan. 2015, doi: 10.1038/nrcardio.2014.160.

G. Montalescot, U. Sechtem, 2013 ESC guidelines on the management of stable coronary artery disease. The Task Force on the management of stable coronary artery disease of the European Society of Cardiology European Heart Journal (2013) 34, 2949-3003, doi:10.1093/eurheartj/eht296.

S. Vijayan, D. S. Barmby, I. R. Pearson, A. G. Davies, S. B. Wheatcroft, M. Sivananthan, "Assessing Coronary Blood Flow Physiology in the Cardiac Catheterisation Laboratory," CCR, vol. 13, No. 3, Jul. 2017, doi: 10.2174/1573403X13666170525102618.

S. Orde, A. McLean, "Bedside myocardial perfusion assessment with contrast echocardiography," Crit Care, vol. 20, No. 1, p. 58, Dec. 2016, doi: 10.1186/s13054-016-1215-7.

D. Maresca, M. Correia, O. Villemain, A. Bize, L. Sambin, M. Tanter, B. Ghaleh, M. Pernot, "Noninvasive Imaging of the Coronary Vasculature Using Ultrafast Ultrasound," JACC Cardiovasc Imaging, vol. 11, No. 6, pp. 798-808, Jun. 2018, doi: 10.1016/j.jcmg.2017.05.021.

B.-F. Osmanski, D. Maresca, E. Messas, M. Tanter, M. Pernot, "Transthoracic ultrafast Doppler imaging of human left ventricular hemodynamic function," IEEE Trans. Ultrason., Ferroelect., Freq. Contr., vol. 61, No. 8, pp. 1268-1275, Aug. 2014, doi: 10.1109/TUFFC.2014.3033.

J. Provost, A. Garofalakis, J. Sourdon, D. Bouda, B. Berthon, et al., "Simultaneous positron emission tomography and ultrafast ultrasound for hybrid molecular, anatomical and functional imaging", Nature Biomedical Engineering, 2018, 2, pp. 85-94. 10.1038/s41551-018-0188-z. hal-01864270z.

M. Correia, D Maresca, G Goudot, O Villemain, a Biz'e, L Sambin, M Tanter, B Ghaleh, M Pernot, "Quantitative imaging of coronary flows using 3D ultrafast Doppler coronary angiography," Phys. Med. Biol., vol. 65, No. 10, p. 105013, Jun. 2020, doi: 10.1088/1361-6560/ab8d78.

C. Errico, J. Pierre, S. Pezet, Y. Desailly, Z. Lenkei, O. Couture, M. Tanter, "Ultrafast ultrasound localization microscopy for deep super-resolution vascular imaging," Nature, vol. 527, No. 7579, pp. 499-502, Nov. 2015, doi: 10.1038/nature16066.

P. Song, J. D. Trzasko, A. Manduca, R. Huang, R. Kadirvel, D. Kallmes, S. Chen, "Improved Super-Resolution Ultrasound Microvessel Imaging With Spatiotemporal Nonlocal Means Filtering and Bipartite Graph-Based Microbubble Tracking," IEEE Trans. Ultrason., Ferroelect., Freq. Contr., vol. 65, No. 2, pp. 149-167, Feb. 2018, doi: 10.1109/TUFFC.2017.2778941.

Y. Hao, Q. Wang, Y. Yang, Z. Liu, Q. He, L. Wei, J. Luo, "Non-rigid Motion Correction for Ultrasound Localization Microscopy of the Liver in vivo," in 2019 IEEE International Ultrasonics Symposium (IUS), Glasgow, United Kingdom, Oct. 2019, pp. 2263-2266, doi: 10.1109/ULTSYM.2019.8925749.

M. R. Lowerison, C. Huang, F. Lucien, S. Chen, P. Song, "Ultrasound localization microscopy of renal tumor xenografts in chicken embryo is correlated to hypoxia," Sci Rep, vol. 10, No. 1, p. 2478, Dec. 2020, doi: 10.1038/s41598-020-59338-z.

F. Lin, S. E. Shelton, D. Espindola, J. D. Rojas, G. Pinton,, P. A. Dayton, "3-D Ultrasound Localization Microscopy for Identifying Microvascular Morphology Features of Tumor Angiogenesis at a Resolution Beyond the Diffraction Limit of Conventional Ultrasound," Theranostics, vol. 7, No. 1, pp. 196-204, 2017, doi: 10.7150/thno.16899.

O. Couture, V. Hingot, B. Heiles, P. Muleki-Seya, M. Tanter, "Ultrasound Localization Microscopy and Super-Resolution: A State of the Art," IEEE Transactions on Ultrasonics, Ferroelectrics, and Frequency Control, vol. 65, No. 8, pp. 1304-1320, Aug. 2018, doi: 10.1109/TUFFC.2018.2850811.

C. Papadacci, E. A. Bunting, E. Y. Wan, P. Nauleau, E. E. Konofagou, "3D myocardial elastography and electromechanical wave imaging in vivo," p. 21, 2018.

C. P. Loizou, C. S. Pattichis, J. D'Hooge, Eds., "Introduction to speckle tracking in cardiac ultrasound imaging," in Handbook of Speckle Filtering and Tracking in Cardiovascular Ultrasound Imaging and Video, Institution of Engineering and Technology, 2018, pp. 571-598.

D. Barbosa, B. Heyde, T. Dietenbeck, D. Friboulet, J. D'Hooge, O. Bernard, "Fast Left Ventricle Tracking in 3D Echocardiographic Data Using Anatomical Affine Optical Flow," in Functional Imaging and Modeling of the Heart, vol. 7945, S. Ourselin, D. Rueckert, and N. Smith, Eds. Berlin, Heidelberg: Springer Berlin Heidelberg, 2013, pp. 191-199.

N. Ouzir, A. Basarab, O. Lairez, J.-Y. Tourneret, "Robust Optical Flow Estimation in Cardiac Ultrasound Images Using a Sparse Representation," IEEE Transactions on Medical Imaging, vol. 38, No. 3, pp. 741-752, Mar. 2019, doi: 10.1109/TMI.2018.2870947.

C.-M. Yu, J. E. Sanderson, T. H. Marwick, J. K. Oh, "Tissue Doppler Imaging: A New Prognosticator for Cardiovascular Diseases," Journal of the American College of Cardiology, vol. 49, No. 19, pp. 1903-1914, May 2007, doi: 10.1016/j.jacc.2007.01.078.

J. Poree, M. Baudet, F. Tournoux, G. Cloutier, D. Garcia, "A Dual Tissue-Doppler Optical-Flow Method for Speckle Tracking Echocardiography at High Frame Rate," IEEE Trans. Med. Imaging, vol. 37, No. 9, pp. 2022-2032, Sep. 2018, doi: 10.1109/TMI.2018.2811483.

R. L. Maurice M. Bertrand, "Lagrangian speckle model and tissue-motion estimation-theory [ultrasonography]," IEEE Transactions on Medical Imaging, vol. 18, No. 7, p. 11, 1999.

W.-N. Lee, J. Provost, K. Fujikura, J. Wang, E. E. Konofagou, "In vivo study of myocardial elastography under graded ischemia conditions," Phys. Med. Biol., vol. 56, No. 4, pp. 1155-1172, Feb. 2011, doi: 10.1088/0031-9155/56/4/017.

Wei-Ning Lee, C. M. Ingrassia, S. D. Fung-Kee-Fung, K. D. Costa, J. W. Holmes, E. E. Konofagou, "Theoretical Quality Assessment of Myocardial Elastography with In Vivo Validation," IEEE Trans. Ultrason., Ferroelect., Freq. Contr., vol. 54, No. 11, pp. 2233-2245, Nov. 2007, doi: 10.1109/TUFFC.2007.528.

V. Hingot, C. Errico, M. Tanter, O. Couture, "Subwavelength motion-correction for ultrafast ultrasound localization microscopy," Ultrasonics, vol. 77, pp. 17-21, May 2017, doi: 10.1016/j.ultras.2017.01.008.

G. Montaldo, M. Tanter, J. Bercoff, N. Benech, M. Fink, "Coherent plane-wave compounding for very high frame rate ultrasonography and transient elastography," IEEE Trans. Ultrason., Ferroelect., Freq. Contr., vol. 56, No. 3, pp. 489-506, Mar. 2009, doi: 10.1109/TUFFC.2009.1067.

B. Dunmire, K. W. Beach, K.-H. Labs, M. Plett, D. E. Strandness, "Cross-beam vector Doppler ultrasound for angle-independent velocity measurements," Ultrasound in Medicine & Biology, vol. 26, No. 8, pp. 1213-1235, Oct. 2000, doi: 10.1016/S0301-5629(00)00287-8.

(56)                    References Cited

OTHER PUBLICATIONS

J. Kirkhorn, "Introduction to IQ-demodulation of RF-data," p. 13, 1999.

C. Kasai, K. Namekawa, A. Koyano, R. Omoto, "Real-Time Two-Dimensional Blood Flow Imaging Using an Autocorrelation Technique," p. 7.

F. L. Bookstein, "Principal warps: thin-plate splines and the decomposition of deformations," IEEE Trans. Pattern Anal. Machine Intell., vol. 11, No. 6, pp. 567-585, Jun. 1989, doi: 10.1109/34. 24792.

K. C. Assi, E. Gay, C. Chnafa, S. Mendez, F. Nicoud, J. F. P. J. Abascal, P. Lantelme, F. Tournoux, D. Garcia, "Intraventricular vector flow mapping—a Doppler-based regularized problem with automatic model selection," Phys. Med. Biol., vol. 62, No. 17, pp. 7131-7147, Aug. 2017, doi: 10.1088/1361-6560/aa7fe7.

Pohiman, Robert M. et al. "Physiological Motion Reduction Using Lagrangian Tracking for Elecirode Dispiacement Elastography." Ultrasound in medicine & biology, vol. 46,3 (2020): 766-781. doi: 10. 1016/j.ultrasmedbio.2019. 11.001.

Shahriari, Shahrokh et al. "Meshfree simulations of ultrasound vector flow imaging using smoothed particle hydrodynainics." Physics in medicine and biology vol. 63,20 205011. Oct. 17, 2018, doi:10.1088/1361-6560/aae3c3.

Umeyama, Motohiko. "Eulerian-Lagrangian Analysis for Particle Velocities and Trajectories in a Pure Wave Motion Using Particle Image Velocimetry." Philosophical Transactions: Mathematical, Physical and Engineering Sciences, vol. 370, No. 1964, Royal Society, 2012, pp. 1687-1702. doi:10.1098/rsta.2011.0450.

Tagliabue, Eleonora et al. "Biomechanical modelling of probe to tissue interaction during ultrasound scanning." International Journal of Computer Assisted Radiology and Surgery, vol. 15, 2020, pp. 1379-1387. doi: 10. 1007/sl1548-020-02183-2.

\* cited by examiner

R-WAVE TRIG

MONITORING PAD

DYNAMIC ACQUISITION

Short axis Bmode

Microbubble Localization

Lagrangian Beamforming and Tissue Filtering

Lagrangian Coordinates Generation

100 μm

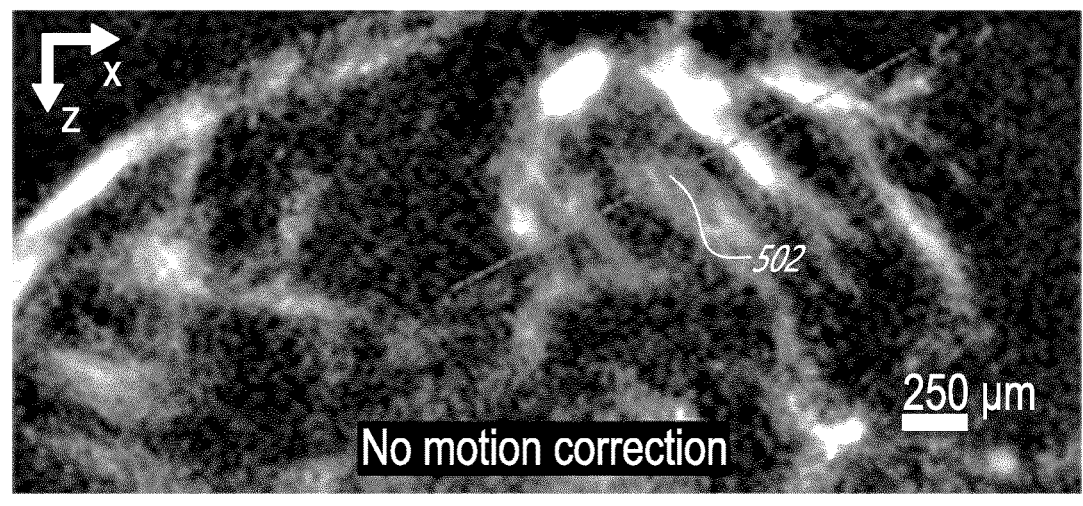
No motion correction
$\boxed{=\!=\!\!=\!\!\!\Box\!\!\!\!=. 5\text{A}}$
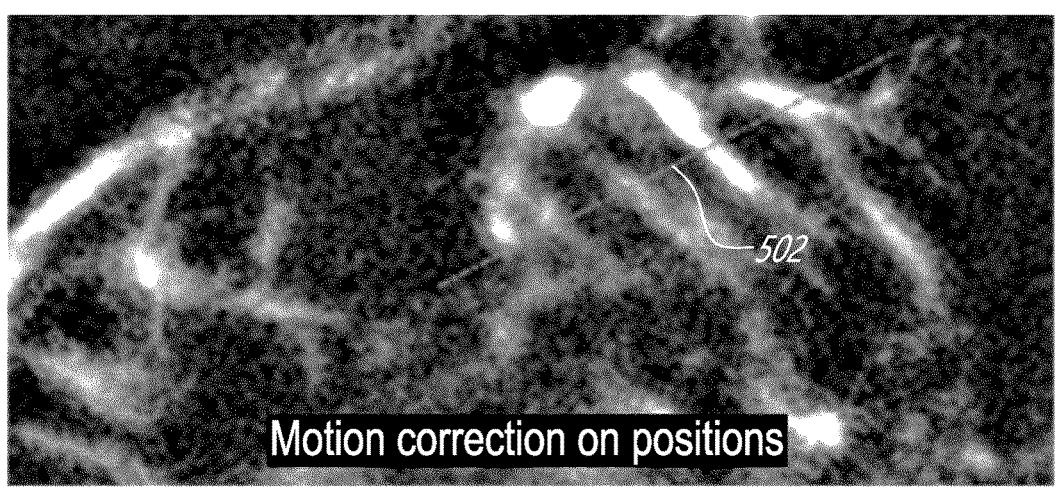
Motion correction on positions
$\boxed{=\!=\!\!=\!\!\!\Box\!\!\!\!=. 5B}$
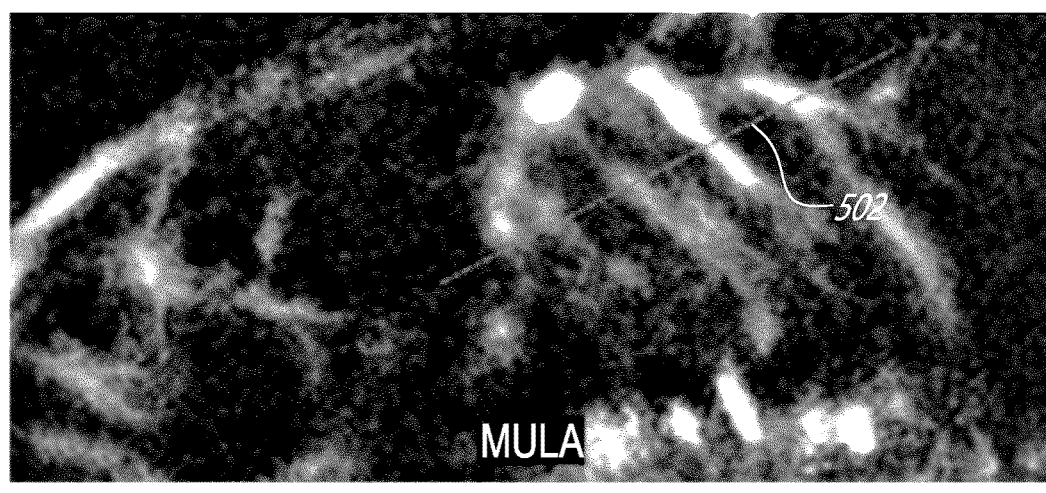
MULA
$\boxed{=\!=\!\!=\!\!\!\Box\!\!\!\!=. 5C}$

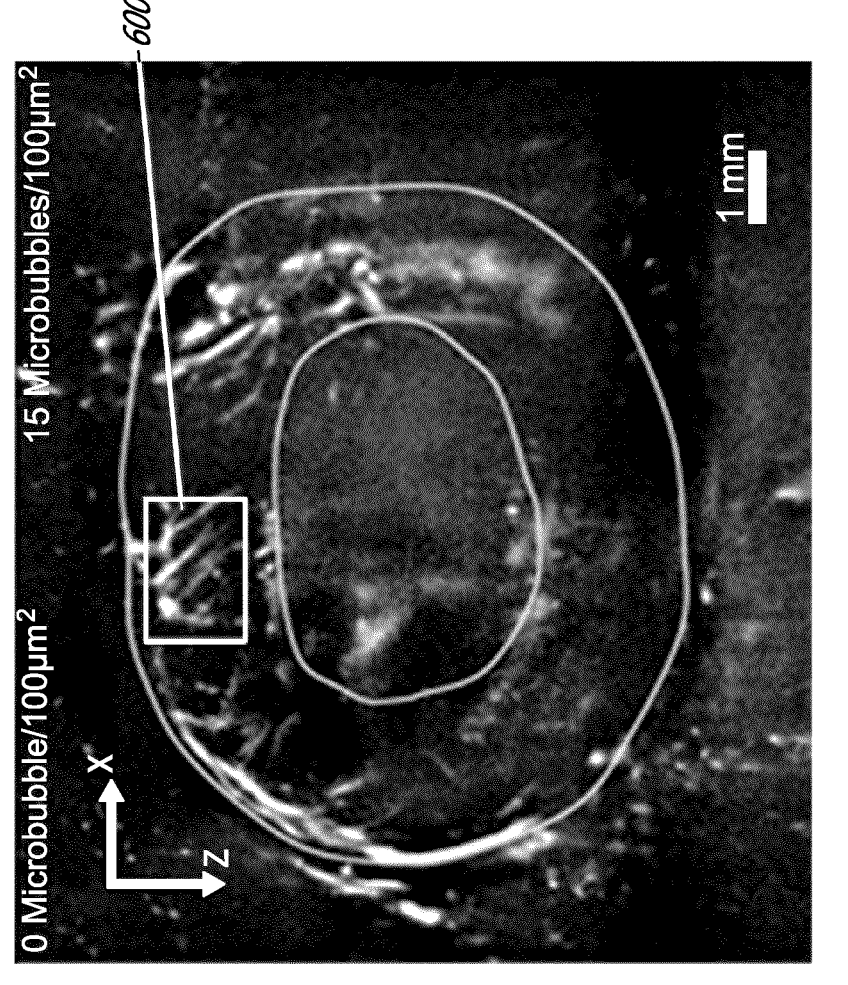
_FIG. 6A_

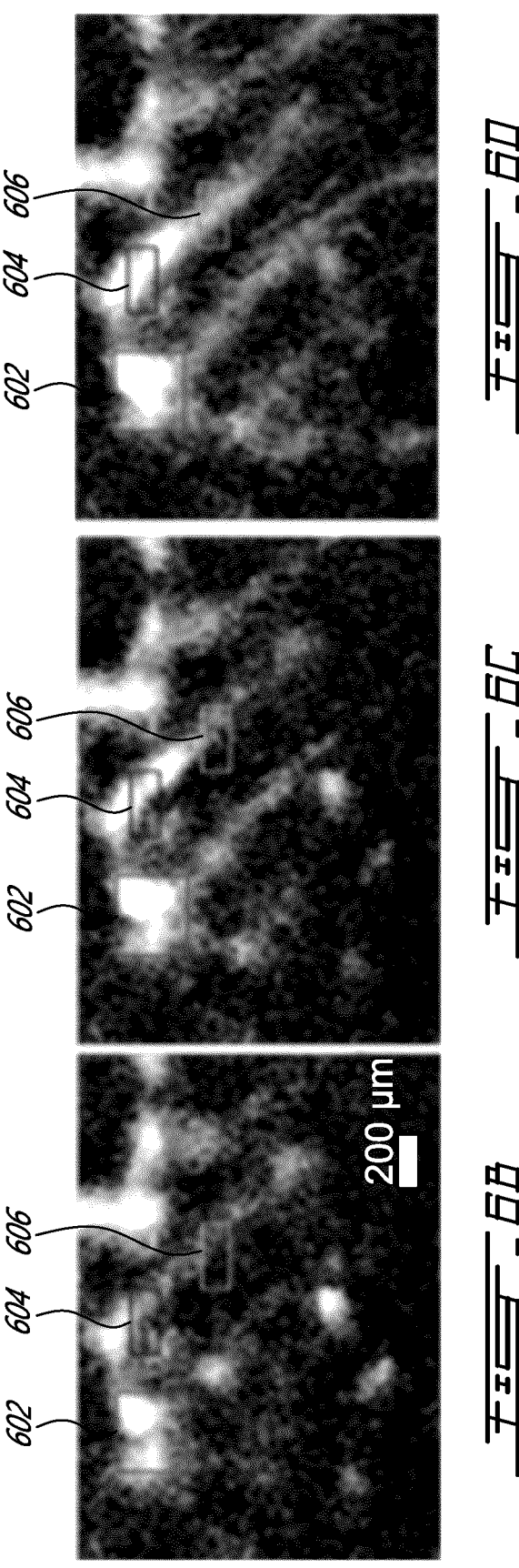
_Fig. 6D_
_Fig. 6C_
_Fig. 6B_

METHODS AND SYSTEMS FOR ULTRASOUND IMAGING OF A BODY IN MOTION

CROSS-REFERENCE TO RELATED APPLICATIONS

The present application is a United States National Stage of International Application No. POT/CA2021/051088, filed on Aug. 5, 2021, which claims the benefit of U.S. Provisional Patent Application No. 63/061,925 filed on Aug. 6, 2020, the contents of which are hereby incorporated by reference in their entirety.

TECHNICAL FIELD

The present disclosure relates generally to ultrasound imaging, and more particularly to ultrasound imaging in the presence of relative motion between a body being imaged and an imaging probe.

BACKGROUND OF THE ART

In patients with known or suspected coronary artery disease (CAD), cardiac imaging tests often constitute the first step in diagnosis and treatment planning. The most typical approach in characterizing CAD focuses on the anatomy of a coronary artery tree by determining which arteries undergo narrowing or obstruction using standard angiography. However, the observed narrowing does not always correlate well with blood flow and the heart function or, more importantly, with the patient's symptoms and prognosis.

The heart's arterial system is composed of three different compartments of dimensionally distinctive vessels having various functions. The large epicardial coronary arteries (~500 μm to ~5 mm) have a capacitance function and flow is subject to little resistance. The intramyocardial vessels, prearterioles (~100-500 μm) and arterioles (<100 μm), have respective functions of pressure regulation and metabolic regulation of the myocardial blood flow (MBF). These structures host the coronary microcirculation and compose the site of coronary microvascular dysfunction (CMD). This is an important mechanism of myocardial ischemia with a high prevalence in patients with suspected CAD. While there are multiple imaging approaches often based on large fixed infrastructure that have been developed to obtain diagnostic and prognostic information non-invasively and through indirect measures, they often suffer from limitations in terms of sensitivity and specificity, which may lead on the one side to an unnecessary coronary angioplasty or on the other side to untreated life-threatening conditions.

Therefore, improvements are needed.

SUMMARY

In accordance with a broad aspect, there is provided a method for ultrasound imaging in presence of relative motion between a body and an imaging probe. The method comprises obtaining a plurality of Eulerian-based ultrasound images of the body acquired at successive times T with the imaging probe, computing Lagrangian coordinates for the body using data from the Eulerian-based ultrasound images, and forming Lagrangian-based ultrasound images of the body by providing the data from the Eulerian-based ultrasound images in the Lagrangian coordinate system.

In some embodiments, computing the Lagrangian coordinates for the body comprises determining Doppler velocities from the Eulerian-based ultrasound images, and converting the Doppler velocities into the Lagrangian coordinates.

In some embodiments, determining the Doppler velocities comprises regularizing the Doppler velocities in time and space by solving a minimization problem.

In some embodiments, converting the Doppler velocities into the Lagrangian coordinates comprises setting the Lagrangian coordinates for a time T to Eulerian coordinates of the Eulerian-based ultrasound images, and estimating a displacement the Eulerian coordinates from the time T to a time T+1 from the Doppler velocities.

In some embodiments, converting the Doppler velocities into the Lagrangian coordinates comprises setting the Lagrangian coordinates for the time T and estimating the displacement of the Eulerian coordinates from the time T to the time T+1 iteratively to regularize the Lagrangian coordinates.

In some embodiments, the body is a biological body.

In some embodiments, the biological body is a heart.

In some embodiments, the relative motion is a periodic motion.

In some embodiments, the times T are synchronized with a cardiac cycle of the heart.

In some embodiments, the method further comprises filtering the Lagrangian-based ultrasound images to locate positions of microbubbles injected into a blood stream in the Lagrangian coordinates.

In some embodiments, the ultrasound imaging is performed for ultrasound localization microscopy.

In accordance with another broad aspect, there is provided a system for ultrasound imaging in presence of relative motion between a body and an imaging probe. The system comprises a processor and a non-transitory computer-readable medium having stored thereon program code executable by the processor for obtaining a plurality of Eulerian-based ultrasound images of the body acquired at successive times T with the imaging probe, computing Lagrangian coordinates for the body using data from the Eulerian-based ultrasound images, and forming Lagrangian-based ultrasound images of the body by providing the data from the Eulerian-based ultrasound images in the Lagrangian coordinate system.

In some embodiments, computing the Lagrangian coordinates for the body comprises determining Doppler velocities from the Eulerian-based ultrasound images, and converting the Doppler velocities into the Lagrangian coordinates.

In some embodiments, determining the Doppler velocities comprises regularizing the Doppler velocities in time and space by solving a minimization problem.

In some embodiments, converting the Doppler velocities into the Lagrangian coordinates comprises setting the Lagrangian coordinates for a time T to Eulerian coordinates of the Eulerian-based ultrasound images, and estimating a displacement the Eulerian coordinates from the time T to a time T+1 from the Doppler velocities.

In some embodiments, converting the Doppler velocities into the Lagrangian coordinates comprises setting the Lagrangian coordinates for the time T and estimating the displacement of the Eulerian coordinates from the time T to the time T+1 iteratively to regularize the Lagrangian coordinates.

In some embodiments, the body is a biological body.

In some embodiments, the biological body is a heart.

In some embodiments, the relative motion is a periodic motion.

In some embodiments, the times T are synchronized with a cardiac cycle of the heart.

In some embodiments, the program code is executable by the processor for filtering the Lagrangian-based ultrasound images to locate positions of microbubbles injected into a blood stream in the Lagrangian coordinates.

In some embodiments, the ultrasound imaging is performed for ultrasound localization microscopy.

Features of the systems, devices, and methods described herein may be used in various combinations, in accordance with the embodiments described herein.

BRIEF DESCRIPTION OF THE DRAWINGS

Reference is now made to the accompanying figures in which:

FIGS. 5A-5C are examples of microbubble density profiles of vessel patterns in different configurations, i.e. no motion correction, motion correction on positions, and MULA, respectively;

FIG. 5D are example curves of microbubble density profiles of the three comparison configurations with the full width half maximum measurement of three vessel patterns;

FIG. 6A is an example of a microbubble density map in the early diastolic period overlaid with the segmentation of the endocardium and epicardium;

FIGS. 6B-6D is an example of an image sequence of microbubble perfusion of vessel patterns within the region of interest;

It will be noted that throughout the appended drawings, like features are identified by like reference numerals.

DETAILED DESCRIPTION

There are described herein methods and systems for ultrasound imaging in the presence of relative motion between a body and an imaging probe. In some embodiments, the body is a biological body, such as tissue or an organ, and the motion is provided by natural movement of the body, for example a cardiac cycle of a beating heart, a respiratory cycle of a lung, or blood flow. In some embodiments, the body is a combination of biological and non-biological, for example microbubbles injected into the blood stream of a subject. In this case, the motion may be a result of the movement of the microbubbles in the blood stream. In some embodiments, the imaging probe is displaced relative to a fixed body, which may be biological or non-biological. For example, the body may be undergoing non-destructive testing using ultrasound imaging and the imaging probe is moved relative to the body.

Figure 1:
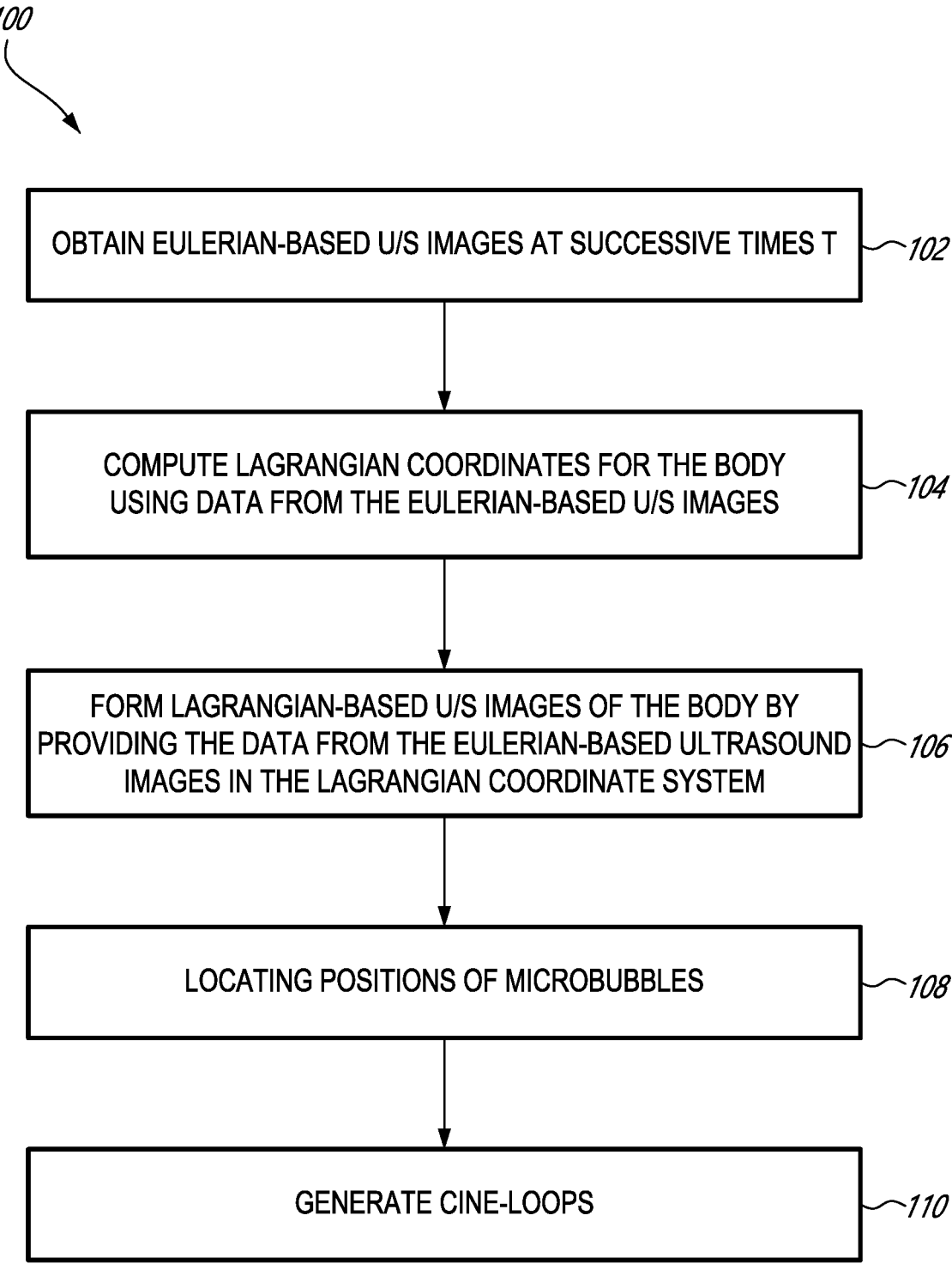
FIG. 1 is a flowchart of an example method for ultrasound imaging.
Figure 2:
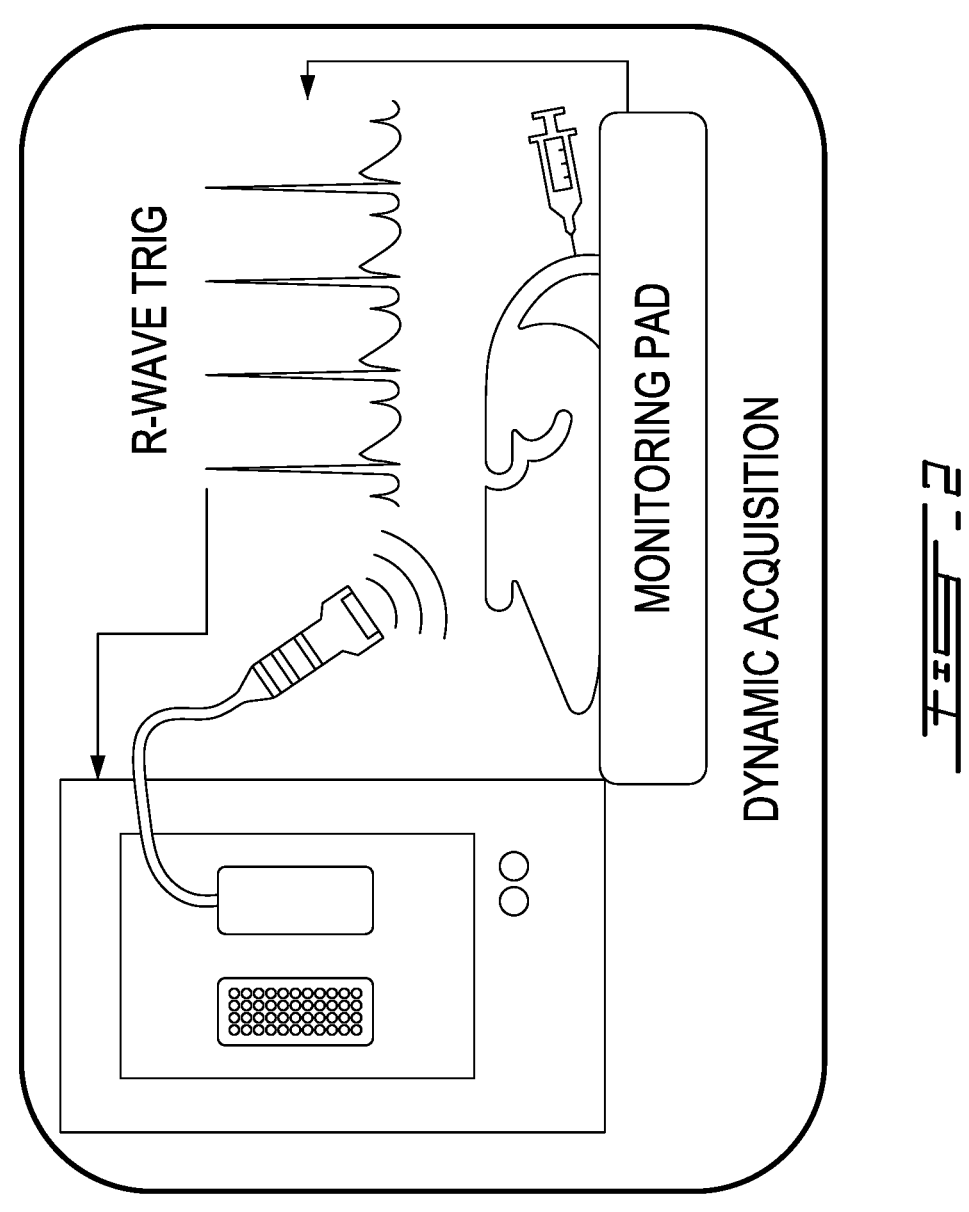
FIG. 2 is a schematic diagram of an example setup for ultrasound imaging.

With reference to FIG. 1, there is illustrated a method 100 for ultrasound imaging in the presence of relative motion. At step 102, a plurality of Eulerian-based ultrasound (u/s) images of the body are acquired at successive times T with an imaging probe. An example is shown in FIG. 2, where a probe is used to obtain u/s images of a subject (e.g. a mouse). In this specific case, a compound plane wave sequence of 3 angles (−3° to 3°) was used to acquire 800 continuous groups of 1200 images at 3000 fps (i.e., 400-ms-long windows) triggered at an R wave of an electrocardiogram (ECG) during a 10-minute period. Each ensemble of 1200 images covering approximately 2.5 heartbeats, was acquired after a minimal pause of 800 ms. In some embodiments, and in the context of myocardial u/s imaging, the exact duration of the pause may be determined by the trigger signal from the ECG and chosen according to data transfer constraints. Alternatively, non-periodic sequences of images may be acquired, with a varying pause between each acquisition.

Referring back to FIG. 1, the data acquired at step 102 is used to form Eulerian-based u/s images. The Eulerian-based u/s images are formed in a fixed coordinate system where a flow field, such as velocity, is represented as a function of a position x and a time t. At step 104, some of the data from the Eulerian-based u/s images is used to compute Lagrangian coordinates for the body. As used herein Lagrangian coordinates refer to coordinates of the body in motion and are also referred to as material coordinates. The Lagrangian coordinates account for the motion of the body over time, and are thus time-independent. Therefore, the Lagrangian coordinates for the body are the same for both the fixed body and the body in motion. At step 106, Lagrangian-based u/s images are formed in the Lagrangian coordinate system using the data from the Eulerian-based u/s images.

In some embodiments, a Lagrangian beamformer is used for steps 104 and 106, as a means of reducing blurring artefacts associated with large body motion. In most ultrasound applications, beamforming is performed using a standard delay-and-sum (DAS) algorithm:

$$S(\vec{x}) = \int RF(\hat{x}_1, \tau(\vec{x}_1, \vec{x})) d\vec{x}_1 \qquad (1)$$

where $\vec{x} = \{x, z\}$ are the Eulerian coordinates of the pixels within the field of view, $\vec{x}_1$ are the coordinates of the elements of the probe and $\tau(\vec{x}_1, \vec{x})$ is the transmit-receive time of flight of the wave front. Because we aim at recovering u/s information in the coordinate system of the body (i.e., as opposed to the probe coordinate system) we introduce a Lagrangian beamformer that can form ultrasound images in the Lagrangian (or material) coordinates:

$$S_{Lag}(\vec{x}_{Lag}) = \int RF(\vec{x}_1, \tau(\vec{x}_1, \vec{x}_{Lag})) d\vec{x}_1 \tag{2}$$

where $\vec{x}_{Lag} = \{x_{Lag} = (x,z,t), z_{Lag}(x,z,t)\}$ are the Lagrangian coordinates of the body as a function of space and time as computed at step 104.

Lagrangian coordinates may be measured using a regularized framework that can map the Lagrangian coordinates $\vec{x}_{Lag}$ of the body from body Doppler velocity measurements. It can be formulated as follows:

$$\vec{x}_{Lag} = \underset{\vec{x}}{\operatorname{argmin}} \left\{ \left\| \frac{d\vec{x}}{dt} - \vec{v}_T(\vec{x}) \right\|^2 \right\} \tag{3}$$

where the body velocity vectors $\vec{v}_T(\vec{x}) = \{v_x, v_z\}$ can be evaluated from body Doppler measurements. Since $\vec{x}$ is non-regular, (3) is evaluated iteratively as it requires the evaluation of $\vec{v}_T$ at $\vec{x}$ that is, at first unknown.

In some embodiments, converting the Doppler velocities into the Lagrangian coordinates comprises setting the Lagrangian coordinates for a time T to Eulerian coordinates of the Eulerian-based ultrasound images and estimating a displacement the Eulerian coordinates from the time T to a time T+1 from the Doppler velocities. Additionally, this may be done iteratively. To do so, we first initialize the Lagrangian coordinates as the Eulerian coordinates:

$$\vec{x}_{Lag}^0 = \vec{x}_{Euler} \tag{4}$$

and iteratively search for the Lagrangian coordinates using:

$$\vec{x}_{Lag}^i = \underset{\vec{x}}{\operatorname{argmin}} \left\{ \left\| \vec{x} - \vec{x}_{Euler} + \int_{t_{ref}}^{t} \vec{v}_T(\vec{x}_{Lag}^{i-1}, t) dt \right\|^2 \right\} \tag{5}$$

where $t_{ref}$ is the reference time from which the Lagrangian coordinates evolves (i.e., at $t = t_{ref}$ we have $\vec{x}_{Lag} = \vec{x}_{Euler}$) and t is defined from the beginning to the end of a cine-loop duration. In some embodiments where the body is a heart, $t_{ref}$ may be chosen as the peak systole to maximize the myocardium's area transverse to the imaging field in the reference frame. The regularized body vector field $\vec{v}_{body}$ may be evaluated using directional Color Doppler, as detailed hereinbelow.

Figure 3A:
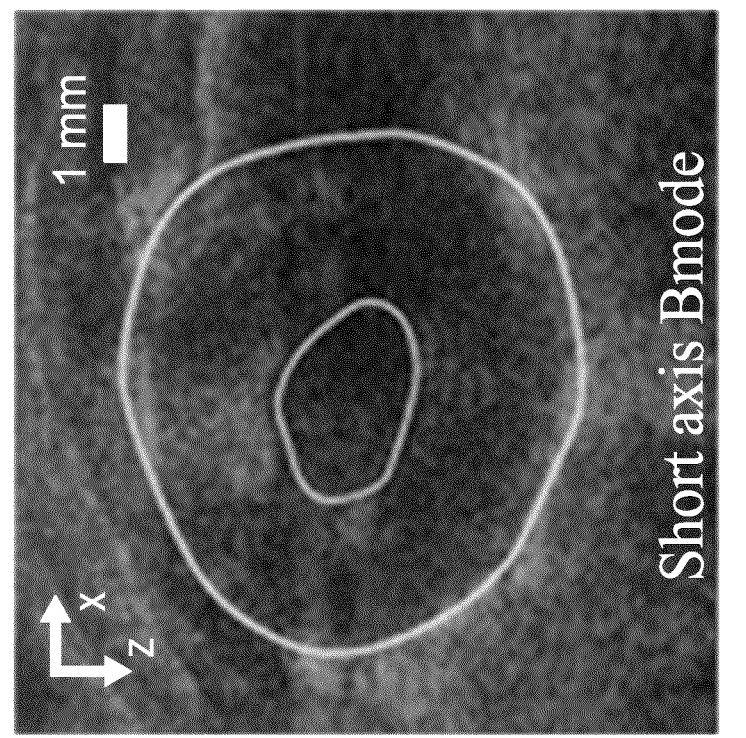
FIG. 3A is an example of delay-and-sum beam-formed images of the left ventricle in parasternal short axis view in the systolic period in brightness mode (Bmode, grayscale) overlaid with a yellow segmentation of the endocardium and epicardium.

Following in-phase quadrature (IQ) demodulation of the raw RF signals and DAS beamforming (see FIG. 3A), a multi-receive-angle $(-5°, 0°, 5°)$ autocorrelation technique may be performed to retrieve directional Doppler shift measurements $\phi_N$. Phase shifts may be converted to Doppler velocities as follows:

$$V_{D_N} = \frac{\lambda f_r \phi_N}{4\pi} \tag{6}$$

where $V_{D_N}$ is the $N^{th}$ angle Doppler velocity, $\lambda$ is the emission wavelength and $f_r$ is the frame rate. Autocorrelation may also be used to formulate a weighting function:

$$\omega_{D_N} = \frac{|R_N(1)|}{R_N(0)} \tag{7}$$

Here $R_N(1)$ and $R_N(0)$ are the lag one and lag zero complex autocorrelations for the $N^{th}$ receive angle, respectively.

The next operations describe how the body velocity field $\vec{v}_T = \{v_x, v_z\}$ may be retrieved from Doppler velocity measurements. In some embodiments, determining the Doppler velocities comprises regularizing the Doppler velocities in time and space by solving a minimization problem. The spatially regularized velocity field $\vec{v}_s$, which may be obtained with the objective of smoothing the velocity field and minimizing noise influence by solving the spatial minimization problem, is referred to as:

$$\vec{v}_s = \underset{\vec{v}}{\operatorname{argmin}} \{J_D(\vec{v}) + \alpha J_{TPS}(\vec{v})\} \tag{8}$$

where $\alpha$ is used to balance the smoothing $J_{TPS}(\vec{v})$ and data fitting $J_D(\vec{v})$ of the functional. $J_D(\vec{v}_s)$ corresponds to the error term between the Doppler measurements and the vector velocity projection onto the Doppler axis. It is defined as follows:

$$J_D(\vec{v}) = \sum_{\theta_N} \int_{\Omega,t} \omega_{D_N} (\vec{d}_{D_N} \cdot \vec{v} - V_{D_N})^2 \tag{9}$$

where $\vec{d}_{D_N}$ is a unit vector describing the Doppler orientation, $\Omega$ is the domain of interest, which includes the entire heart and $\theta_N$ are the selected Doppler orientations.

To ensure the spatial continuity of the velocity field, and hence the spatial continuity of the Lagrangian grid, a thin plate spline regulator may be used, defined as:

$$J_{TPS}(\vec{v}) = \sum_{i=(x,z)} \int_{\Omega,t} (\partial_{xx} v_i)^2 + 2(\partial_{xz} v_i)^2 + (\partial_{zz} v_i)^2 \tag{10}$$

To ensure the temporal continuity of the velocity field and prevent drifting artefacts, a temporal regulator is introduced that is the weighted sum of the first order temporal derivative and a periodic derivative. It may be defined as follows:

$$J_{regt}(\vec{v}) = \alpha_t \int_{\Omega,t} \|\partial_t \vec{v}\|^2 + \alpha_T \int_{\Omega,t} \|\partial_T \vec{v}\|^2 \tag{11}$$

where $\partial_t$ at is a temporal derivative operator and $\partial_T$ is a periodic derivative operator computing the slope between an instant and it's periodic following, which, in some cases, corresponds to a heartbeat period (i.e., T=1/HeartRate), hence enforcing the velocity field to be reproducible between heartbeats. The $\alpha_t$ and $\alpha_T$ coefficients may be respectively chosen to weight the temporal and periodic smoothing.

The spatiotemporal regularized vector velocity field $\vec{v}_{st}$ may be found by solving the following minimization problem:

$$\vec{v}_{st} = \underset{\vec{v}}{\mathrm{argmin}}\left\{ \int_{\Omega,t} \omega_D \|\vec{v} - \vec{v}_s\|^2 + J_{regt}(\vec{v}) \right\} \tag{12}$$

where $\omega_D$ is the Doppler autocorrelation weighting function $\omega_{D_N}$ averaged over Doppler orientations and $\hat{v}_s$ is the spatially regularized vector velocity field.

Figures 3B, 3C, 3D:
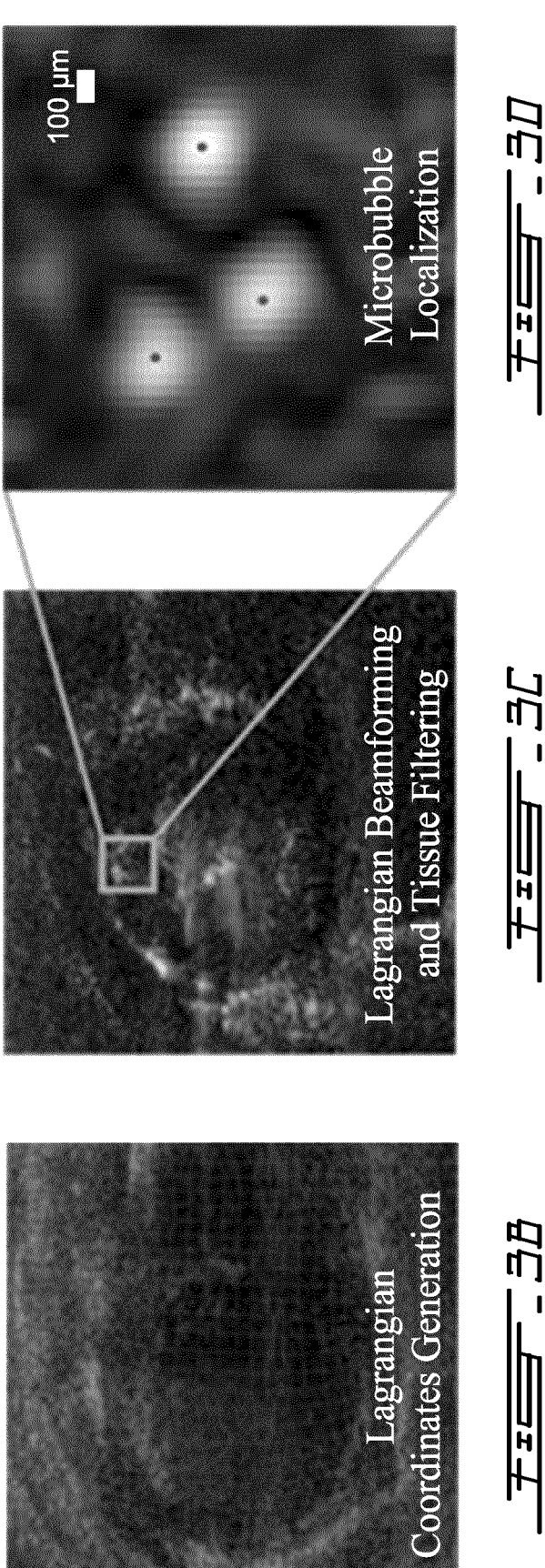
FIG. 3B is an example of Lagrangian coordinates of the diastolic period in a grid overlaid on the B-mode image.
FIG. 3C is an example of Lagrangian beam-formed images processed through a time-dependent SVD tissue filter to isolate microbubble signal.
FIG. 3D is an example of a 2D point spread function kernel correlated with the filtered images followed by a 2D gaussian peak fitting to localize microbubble centroids.
Figures 3E, 3F:
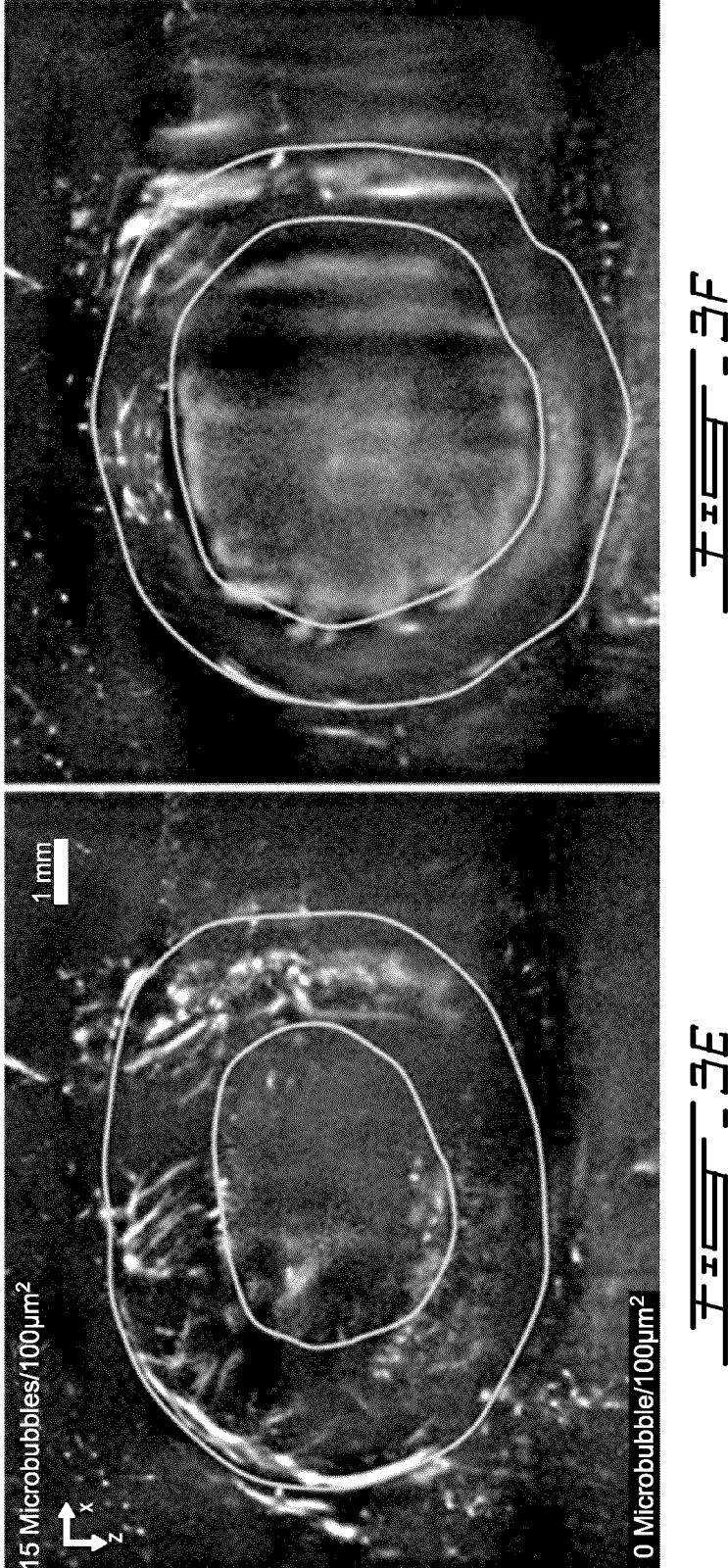
FIGS. 3E-3F are examples of microbubble centroids accumulated in 17 ms sliding windows to create density maps in early and end diastole, respectively.

The following step was used to convert velocity fields into Lagrangian coordinates by integration as a solution of the equation (3). The key concept here was to implement motion within the imaging plane's mesh (FIG. 3B). This mesh was initialized as a Eulerian grid whose origin was set at the center of the aperture. The mesh was then updated iteratively using (5).

Approximate solutions to the minimization problems described in (8) and (12) may be computed over a cartesian grid. The algorithm may be implemented through the following steps:

1. Retrieve Doppler velocities, directions and weighting functions through autocorrelation
2. Build vectors and matrix operators for the numerical representation of the functionals
3. Solve the spatial regularization least squares problem (8).
4. Solve temporal regularization least squares problem (12).
5. Compute Lagrangian coordinates $$\vec{x}_{Lag}^i$$

6. Evaluate Doppler Velocities and directions in Lagrangian coordinates (i.e., $$V_{D_N}(\vec{x}_{Lag}^i, t))$$

)

7. Repeat steps 2-6 to regularize the problem in Lagrangian coordinates.

In practice, Lagrangian coordinates may be sufficiently stable after 3 iterations but more than 3 iterations may also be used.

In some embodiments, the ultrasound imaging is performed with the context of Ultrasound Localization Microscopy (ULM). ULM consists of locating, tracking and accumulating highly echogenic, individual microbubbles (MB) within the vasculature. ULM overcomes the diffraction limit and enables sub-wavelength resolution of vascular pathways. The method 100 relies on solutions to reduce motion artefacts in the ULM process and enable dynamic imaging of micro vessels' blood flow. First, ultrasound images are acquired by successive time ensembles, which are compatible in the referential of the ECG signal. Images are reconstructed through a Lagrangian beamformer which corrects for the large non-rigid motion before tissue filtering and MB localization. MB positions are then accumulated in a 2D+t MB density matrix to generate a subwavelength resolved vessel cine-loop.

As shown in FIG. 1, the positions of microbubbles injected in to the blood stream may be determined by filtering the Lagrangian-based u/s images at step 108. In one specific and non-limiting example, following beamforming, a time-dependent spatiotemporal filter consisting of a 17-ms (or, 50-frame) sliding window Singular Value Decomposition (SVD) filter may be applied to extract MBs, for each image ensemble. The SVD-filtered images are then correlated to a simulated point spread function (PSF) to locate MB positions. Subwavelength centroids are retrieved using a 2D Gaussian fitting of the correlation map local peaks. At step 110, cine-loops are then generated by accumulating the centroids of within 17-ms sliding temporal windows in a 10-μm MB density map, see FIGS. 3C-3F.

To quantify the performance of the method 100, images were developed from a conventional DAS beamformer where the localization process was then applied leading to a motion present cine-loop of the MB density map. As additional means of comparison, a second opportunity for motion correction is proposed. This alternative technique consists in the modification of the localized MB positions from the DAS approach with respect to the measured body motion retrieved by the algorithm described herein. The computation of the motion corrected localizations is made through a similar process as the material coordinates generation. The position of motion corrected MBs is given by:

$$\vec{x}_{MB,MoCo_t} = \vec{x}_{MB_t} \int_{t_{reference}}^{t} \vec{v}dt \tag{13}$$

where the measured tissue displacement is subtracted from the MB position $\vec{x}_{MB_t}$. The comparison method relies on a vessel profile analysis. This was done by demarcating the same vessel structures in the density maps of each comparison configurations and MULA, then measuring the full width half maximum (FWHM) of the structures.

Figures 4A, 4B:
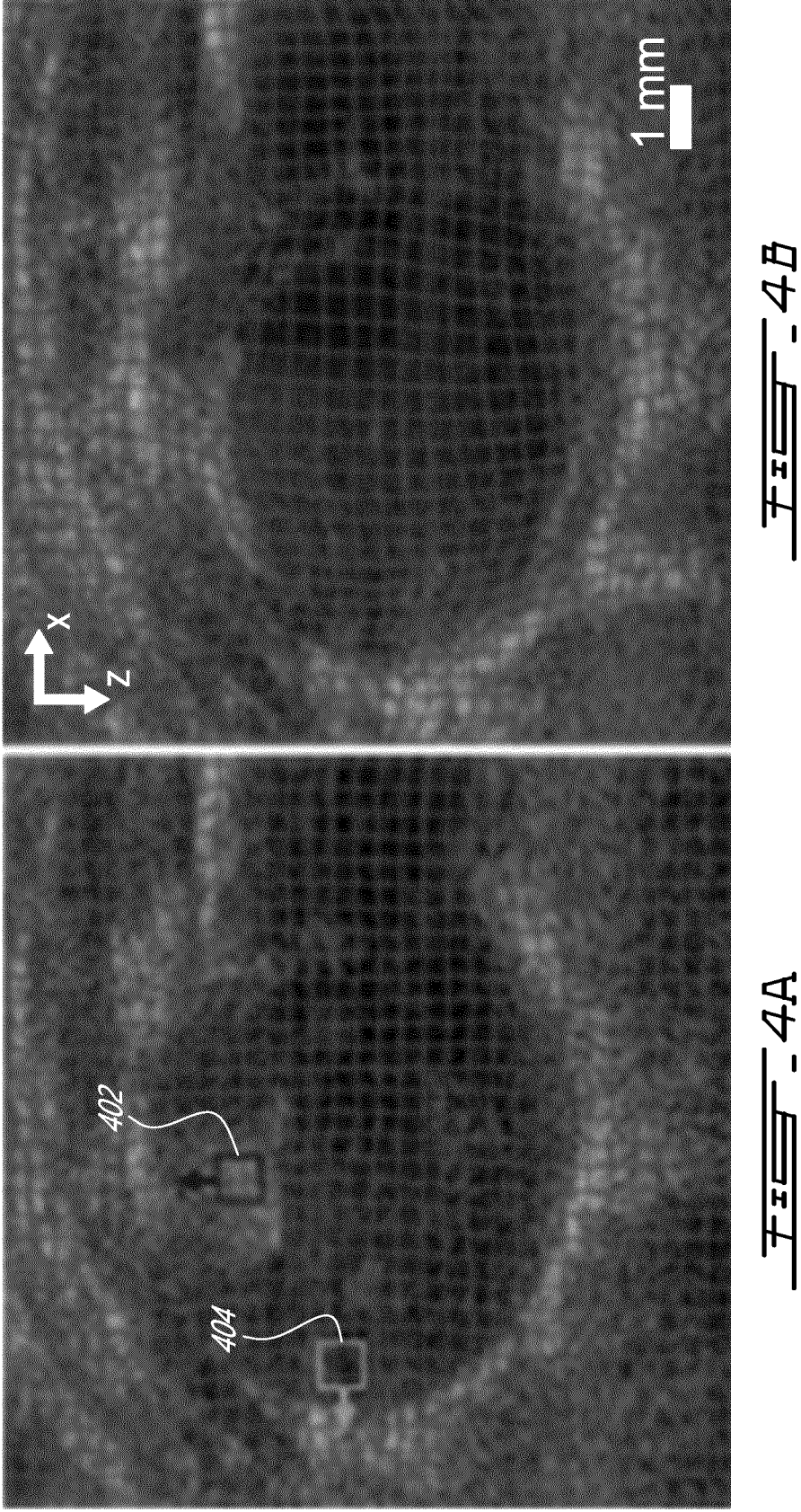
FIGS. 4A-4B are examples of a Lagrangian coordinates grid overlaid on B mode images (grayscale) of the left ventricle in the systole period and diastole period, respectively.
Figure 4C:
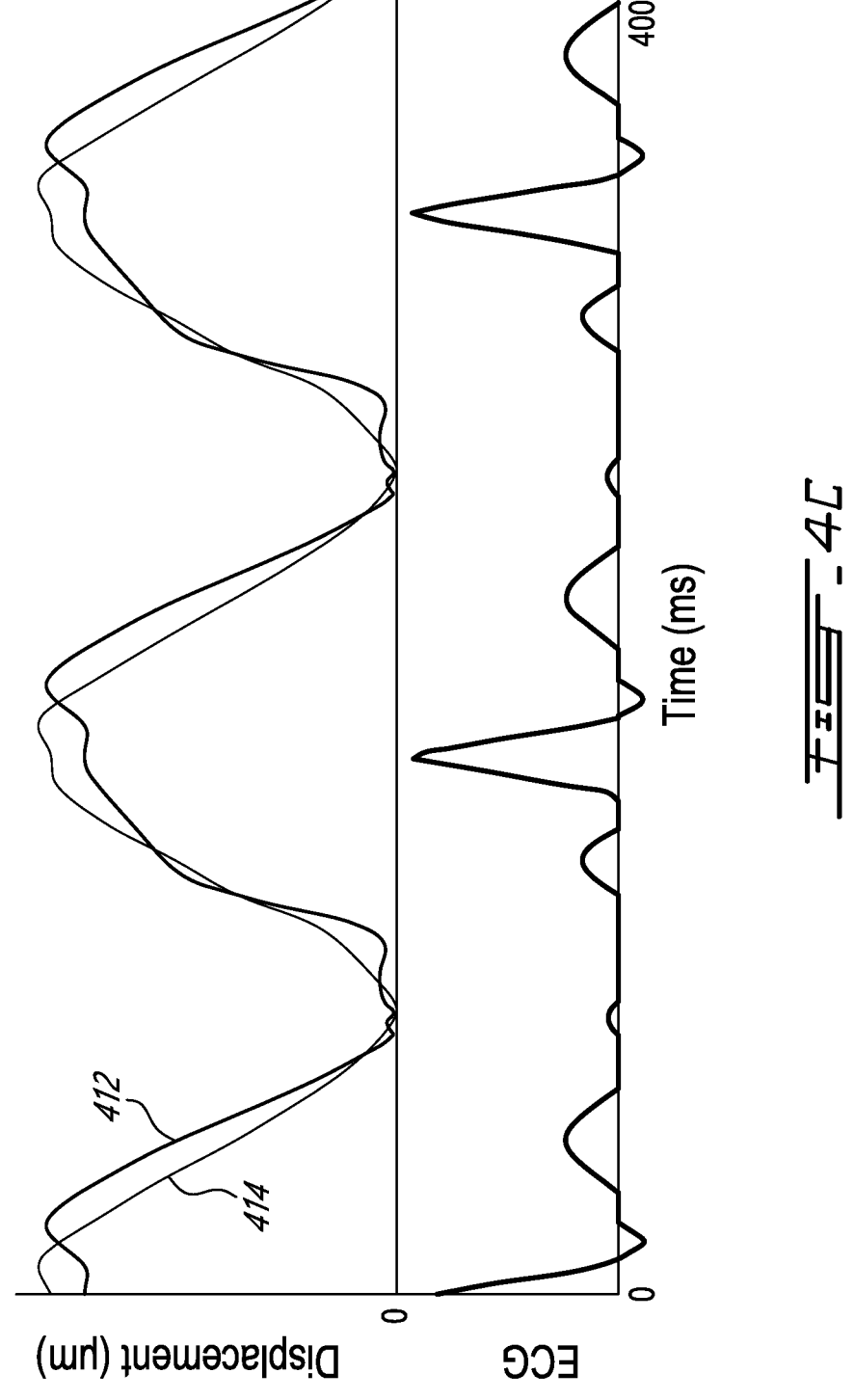
FIG. 4C are examples of curves of displacement respective to the peak systolic period shown through the heartbeat cine-loop, and a simulated electrocardiogram for illustration purposes.
Figure 50:
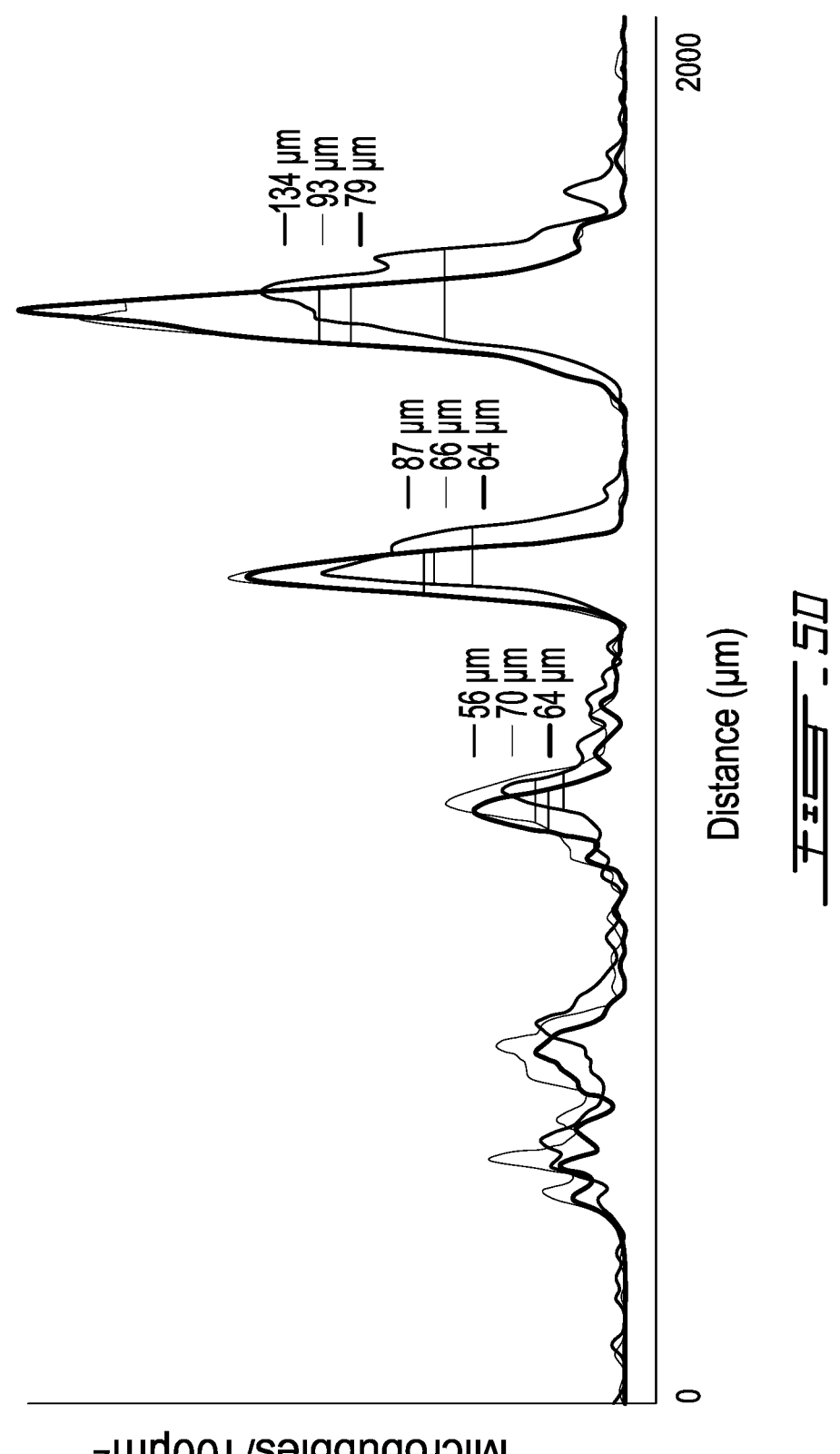

FIGS. 4A-4C display the Lagrangian coordinates grid's behavior through the heartbeat cine-loop. The coordinates (the grid) are shown to follow a dilation pattern from systole to diastole (FIGS. 4A-$B). The regions of interest 402, 404 (FIG. 4A) are used to respectively measure vertical and lateral displacements of the Lagrangian coordinates and are located at a few hundreds of μm from the endocardium. The top portion of FIG. 4C presents the average displacements 412, 414 within the ROIs 402, 404 respectively, relative to the reference of the Lagrangian grid (systole period) as a function of time. Peak mean displacement measurements are 490 μm laterally and 480 μm axially. Additionally, a simulated electrocardiogram (FIG. 4C, bottom portion) shows the dynamic evolution of the Lagrangian coordinates. It enables the visualization of temporal and spatial smoothness of the grid, the periodic behavior and the different patterns in the motion: dilation, contraction and curl.

To assess the differences between the proposed method 100 and comparison configurations (described below), a line 502 was drawn in the images of FIGS. 5A-5C, intersecting vessel patterns emerging from a treelike structure on the MB density maps of each comparison configuration in the early diastolic period. Three transverse vessel profiles were selected for analysis based on their amplitude and well-defined peaks. FIG. 5D shows the projection of the density maps on the line for all configurations. For the two largest vessel profiles on the right end of the line 502, the method 100 leads to a full width at half maximum (FWHM) measurement which is 39% smaller (134 μm to 81 μm) and 28% smaller (89 μm to 64 μm) with higher peaks than the approach without motion correction. For the third vessel, the scenario without motion correction denotes the smallest FWHM but again with a lower peak. In the case where the positions of MB were corrected, FWHM measurements of 70, 66 and 93 μm were obtained.

Several vessel patterns were localized within the intramyocardial region in an MB density cine-loop produced by the method 100 projected on Eulerian coordinates. The vessel patterns were seen pulsing periodically in various regions of the imaging plane with each heartbeat. The arrangement of these vessels varies through the heart cycle. Globally, few larger vessels are clearly shown emerging from the epicardium and remain discernable through most of the heartbeat cycle. They spread downwards in smaller networks of more numerous vessels crossing the myocardial wall to the endocardium, which are mostly present when the myocardial wall is contracted. The size of the vessel patterns located in the myocardium varied from 60 to 200 μm and were more numerous in the anterior section of the myocardium (top half of the imaging plane).

Figure 6E:
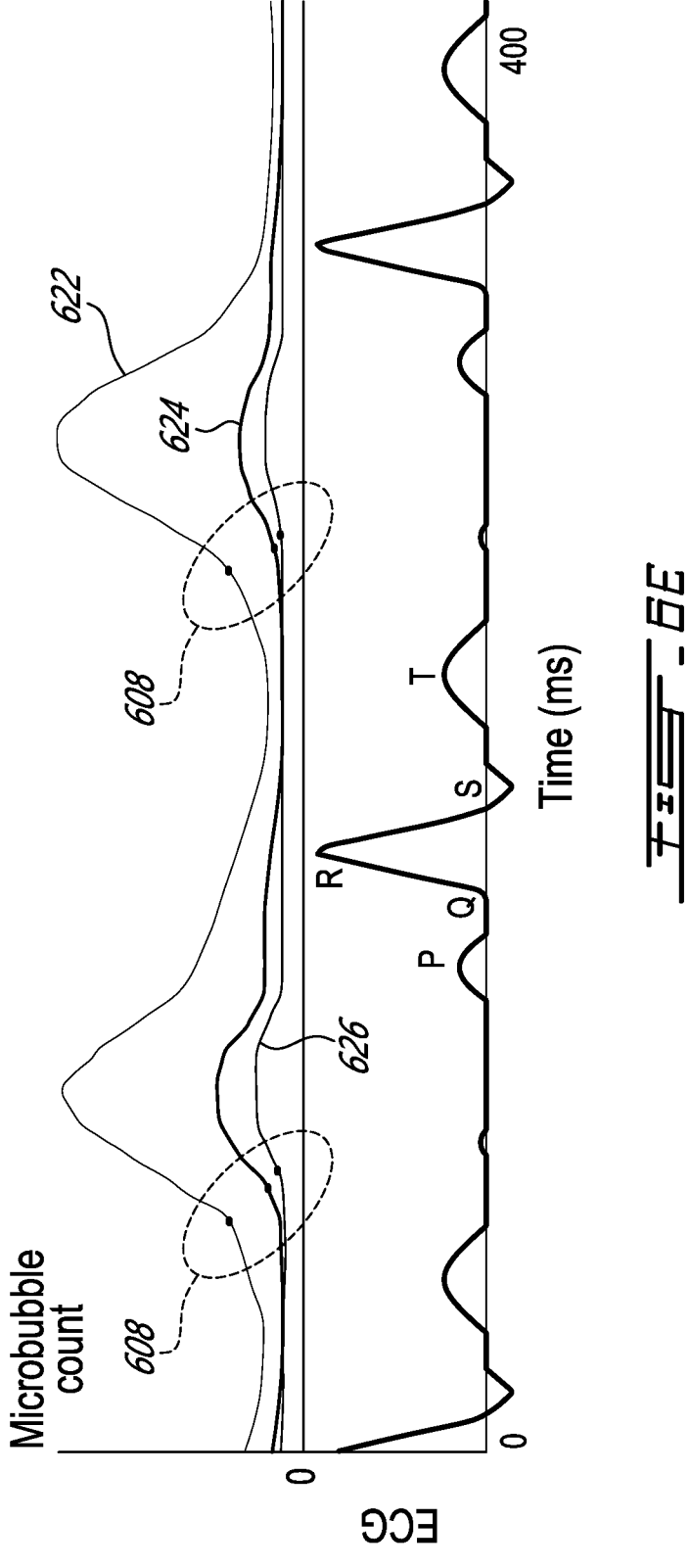
FIG. 6E are example curves of a dynamic evolution of microbubble density within each sub region of interest through the heartbeat cine-loop, and a simulated electrocardiogram shown as temporal reference.

In FIGS. 6A-6E, the method 100 was used to measure dynamic flow parameters of a vessel pattern. The region 600 in FIG. 6A delimits the ROI of the analysis, which is a posterior section of the left ventricle wall. Within the ROI, the 3 sub-regions shown in FIGS. 6B-6D represent a proximal 602, intermediate 604 and distal 606 portion of a vessel pattern relative to the epicardium. The image sequence of the ROI is shown at 25% of the upstroke for each sub region which are measured by taking 25% of the microbubble filling peak within the sub-regions. Moreover; the portion 602 includes a proximal large transversal section, the portion 604 includes the top section of an underlying vessel pattern (intermediate) and the portion 606 includes a deeper portion of the same vessel pattern (distal). The 25% upstroke timings (608 in FIG. 6E) in the chronological order are the following: 64 ms (proximal, 422), 73 ms (intermediate, 424) and 77 ms (distal, 426I) for the first heartbeat of the cine-loop and 243 ms (proximal, 422), 249 ms (intermediate, 424) and 253 ms (distal, 426) for the second heartbeat of the cine-loop. The bottom portion of FIG. 6E is a simulated electrocardiogram shown as a temporal reference.

There is described herein the feasibility of the method 100 to map features of a body such as blood vessels with a subwavelength resolution in presence of large motion within the myocardial wall. The chosen approach of an ECG-gated acquisition paired with a motion correction algorithm, which corrects for the heart motion, has enabled the imaging of the angio-architecture and hemodynamics of the intramyocardial microvasculature. The method 100 was successful at correcting for the displacements of the tissue during the entire heart cycle.

The implementation of the method 100 was based on numerous parameters and configuration choices. Some of the analysis was made by iterating the smoothing and weighting parameters and observing the velocity fields and material coordinates overlaid on B mode films. Since the left ventricle cavity was an important portion of the imaging field and had no coherent tissue information due to its blood composition, a threshold was imposed on the pixel-wise weighting parameter to suppress it's influence in the algorithm. This condition was automatically transposed to all regions with smaller correlation.

As shown in FIGS. 4A-4B, the reference material coordinates grid was set for the systolic state and the grid follows dilation and constriction movements of the heart. FIG. 4C shows how the periodicity of the beating heart was well reproduced by the method 100. The method 100 has successfully performed the registration of both axial and lateral tissue motion since the magnitudes are similar, as expected in a short-axis view. The displacements clearly follow the ventricular systolic period, which lasts from the peak of the R wave to the end of the T wave, followed by a dilation period completing the ECG cycle, which is the ventricular diastole. On the point of view of the displacement's amplitude, the method 100 has led to peak displacements of 490 μm laterally and 480 μm axially. As means of comparison, peak-to-peak axial displacement from the constricted to dilated state is approximately 1 mm for the endocardium and 500 μm for the epicardium.

The method 100 may comprise the coherent accumulation of the MB positions over time. The performance of two different motion compensation methods was compared. Vessel maps without any motion compensation led to these observations: 1) The myocardial movement drives the blood vessels to move in space over the heartbeat cycle, which will induce large blurring effects when compounding periods of time to build vessel maps. 2) Since the tissue is in motion, implementing a clutter filter based on SVD is challenging due to the similarity in temporal behaviors of the perfusion of MBs and the myocardial motion. The method 100 may be used to form cine loops with large motion correction. Vessel maps were analyzed, where motion correction was applied on the final localization of MBs from a conventional DAS beamforming. As shown in FIGS. 5A-5D, all configurations are compared for a vessel map formed with 200 frames (which represents approximately 67 ms of the cine-loop) in the early diastole. The resolution of vessels was positively affected by the motion compensation: FWHM of vessels provided by the method 100 were approximately 30% smaller than without any motion correction. By performing the comparison method of motion correction on MB positions, it is confirmed that the method 100 is primitively compensating the motion effects through the Lagrangian beamformer. Also, the results provided by the method 100 do seem to have a better contrast, which may be caused by the improved tissue filtration of the motion corrected images. This may explain why FWHM results coming from the method 100 are on average 9% smaller than the alternate motion correction on localizations scenario. In terms of further clinical application of this modality, the motion correction approach is the logical path to follow. Being able to compound larger portions of the heartbeat cycle to create vessel maps would speed acquisition times but would decrease the temporal resolution. However, obtaining better resolved vessels through the Lagrangian beamformer can improve the sensibility of the tool. Secondly, being able to filter efficiently the organ's tissue decreases the time to build well defined vessel maps, since it can positively influence the contrast to noise ratio. In conclusion, the Lagrangian beamformer has allowed substantial improvements of the vessel cine loops over the heartbeat cycle.

Accumulating the MB centroids over short periods of time (i.e., 50 ms) enables vessel patterns to emerge in various sections of the imaging field. Early moments of the dilation movement of the heart muscle have greater MB presence, which can be correlated with flow. When comparing this period with B mode images, M mode images and the ECG signal, this instant represented the early diastolic phase. Hence, static images recreated from this period have greater information on the angio-architecture of the myocardium. The range of dimensions of imaged intramyocardial vessels, which goes from 60 μm to 200 μm, correlates with the size of prearterioles and arterioles contained within the myocardial wall. Structures as small as 40 μm in diameter may be depicted. Mostly larger vessels were detected in the epicardial region, which confirms that this region is feeding the concentric profiles aimed towards the left ventricle cavity. Therefore, this behavior is coherent with the perfusion cycle of the heart where the large epicardial coronary arteries feed the downstream myocardial arterioles and capillaries. For further use of our proposed approach to generate vascular maps, the selection of specific heartbeat cycle periods where vessels look sharper and denser could be considered to make a static angioarchitecture analysis, but it was acknowledged that remaining tissue motion paired with the perfusion behavior of cardiac vessels is challenging the MB accumulation process through the complete heartbeat cycle. The dimension of the vessels detected by the method 100 and their configuration suggest that the method 100 is able to recover the intramyocardial microvasculature.

Adjacent to the ability to image the angio-architecture of the microvasculature, the method 100 may be used to investigate dynamic properties of the intramyocardial blood flow. The analysis of cine-loops generated by the method 100 was made by investigating the myocardium through the heartbeat cycle. As previously mentioned, the configuration and size of vessels suggests a perfusion from larger epicardial vessels toward the myocardial microvasculature. This behavior is also observed in the whole left ventricle wall during the heartbeat cine-loop. The flow, which was here represented by MB density variation, arrived firstly to the epicardium and then propagated to deeper intramyocardial structures. FIGS. 6A-6E confirm this behavior for a well-defined vessel tree: the subregion proximal to the epicardium (602, 622) reaches 25% of upstroke 9 ms before the intermediate subregion (604, 624) which is 4 ms before the distal subregion (606, 626). This sequential order is globally maintained in the second heartbeat of the cine-loop (6 ms proximal-intermediate, 4 ms intermediate-distal). The coherence between the myocardial perfusion and the ECG signal may also be observed. The ventricular diastole, which goes from the end of the T wave to the peak of the R wave, seems to host the large majority of the perfusion of the analyzed intramyocardial ROI. This behavior is physiologically expected, as the heart starts dilating in the early diastole there is a pressure drop in the aorta which allows the perfusion of the coronary vasculature. Secondly, the intramyocardial vessels are compressed and restrain flow during systole due to high ventricular pressure. They are subject to lower pressure and are freed of compression during the diastolic period, which allows for perfusion.

Testing was performed in accordance with the Animal Research Ethics Committee of the Montreal Heart Institute (Permit: 2018-32-03). 3 Sprague-Dawley anesthetized rats (1,5-2,5% isoflurane) with depilated chests were placed on a monitoring platform (LabeoTech, CA) in a supine position to acquire ultrasound images. To minimize global displacements, fixed foam stabilizers were positioned in the periphery of the thorax. After injection of a 10-μL bolus (~1.2× 10^8) of Definity MBs (Lantheus, USA), an ultrasound sequence was launched using a Vantage imaging system (Verasonics, USA) and a L22-14 probe.

Figure 7:
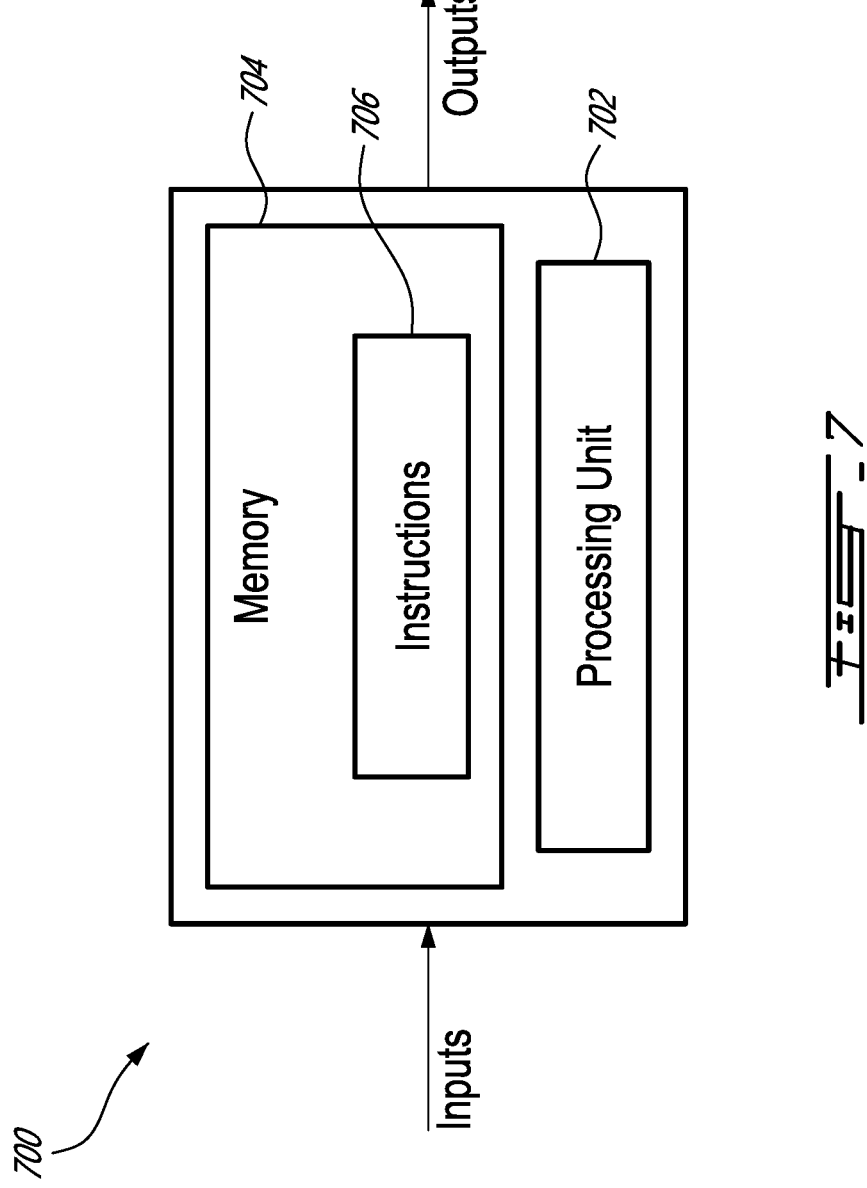
FIG. 7 is a block diagram of an example computing device.

In some embodiments, the method 100 may be performed, in part or in whole, using a computing device 700 as illustrated in FIG. 7. It should be noted that the computing device 700 may be implemented as part of an imaging device. In some embodiments, the imaging device is implemented by the computing device 700. In some embodiments, the computing device 700 is within the imaging device and cooperates with other hardware and/or software components therein. In such cases, the imaging device generates the ultrasound images.

The computing device 700 comprises a processing unit 704 and a memory 704 which has stored therein computer-executable instructions 706. The processing unit 702 may comprise any suitable devices configured to cause a series of steps to be performed such that instructions 706, when executed by the computing device 700 or other programmable apparatus, may cause functions/acts/steps described herein to be executed. The processing unit 702 may comprise, for example, any type of general-purpose microprocessor or microcontroller, a digital signal processing (DSP) processor, a CPU, an integrated circuit, a field programmable gate array (FPGA), a reconfigurable processor, other suitably programmed or programmable logic circuits, or any combination thereof.

The memory 704 may comprise any suitable known or other machine-readable storage medium. The memory 704 may comprise non-transitory computer readable storage medium, for example, but not limited to, an electronic, magnetic, optical, electromagnetic, infrared, or semiconductor system, apparatus, or device, or any suitable combination of the foregoing. The memory 704 may include a suitable combination of any type of computer memory that is located either internally or externally to device, for example random-access memory (RAM), read-only memory (ROM), electro-optical memory, magneto-optical memory, erasable programmable read-only memory (EPROM), and electrically-erasable programmable read-only memory (EE-PROM), Ferroelectric RAM (FRAM) or the like. Memory 704 may comprise any storage means (e.g., devices) suitable for retrievably storing machine-readable instructions 706 executable by processing unit 702.

The method 100 may be implemented in a high-level procedural or object oriented programming or scripting language, or a combination thereof, to communicate with or assist in the operation of a computer system, for example the computing device 700. Alternatively, the method 100 may be implemented in assembly or machine language. The language may be a compiled or interpreted language.

Embodiments of the method 100 may also be considered to be implemented by way of a non-transitory computer-readable storage medium having a computer program stored thereon. The computer program may comprise computer-readable instructions which cause a computer, or more specifically the processing unit 702 of the computing device 700, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically, the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the systems and methods described herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be apparent to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for ultrasound imaging in presence of relative motion between a biological body and an imaging probe, the method comprising:

obtaining a plurality of Eulerian-based ultrasound images of the biological body acquired with the imaging probe at successive times T during an entire cycle of natural movement of the biological body;

computing Lagrangian coordinates for the biological body using data from the Eulerian-based ultrasound images, the Lagrangian coordinates accounting for motion of the biological body over time during the entire cycle of natural movement of the biological body, wherein computing the Lagrangian coordinates for the biological body comprises:

determining Doppler velocities from the Eulerian-based ultrasound images, comprising regularizing the Doppler velocities in time and space by solving a spatial minimization problem and a temporal minimization problem; and converting the Doppler velocities into the Lagrangian coordinates;

forming, using a Lagrangian beamformer, Lagrangian-based ultrasound images of the biological body in the Lagrangian coordinates by providing the data from the Eulerian-based ultrasound images in the Lagrangian coordinate system, the Lagrangian beamformer configured to provide correction for the motion during the entire cycle of natural movement of the biological body; and filtering the Lagrangian-based ultrasound images to locate, throughout the entire cycle of natural movement of the biological body, positions of microbubbles injected into a blood stream.

2. The method of claim 1, wherein converting the Doppler velocities into the Lagrangian coordinates comprises:

setting the Lagrangian coordinates for a time T to Eulerian coordinates of the Eulerian-based ultrasound images; and estimating a displacement of the Eulerian coordinates from the time T to a time T+1 from the Doppler velocities.

3. The method of claim 2, wherein converting the Doppler velocities into the Lagrangian coordinates comprises setting the Lagrangian coordinates for the time T and estimating the displacement of the Eulerian coordinates from the time T to the time T+1 iteratively to regularize the Lagrangian coordinates.

4. The method of claim 1, wherein the biological body is a heart.

5. The method of claim 1, wherein the relative motion is a periodic motion.

6. The method of claim 4, wherein the times T are synchronized with a cardiac cycle of the heart.

7. The method of claim 1, wherein filtering the Lagrangian-based ultrasound images to locate the positions of the microbubbles comprises:

applying a sliding window Singular Value Decomposition (SVD) filter to the Lagrangian-based ultrasound images to obtain SVD-filtered images; and correlating the SVD-filtered images to a simulated point spread function (PSF) to locate the positions of the microbubbles.

8. The method of claim 1, wherein the ultrasound imaging is performed for ultrasound localization microscopy.

9. The method of claim 1, wherein the spatial minimization problem is defined to minimize a noise influence in a velocity field of the Doppler velocities and to apply a spatial smoothing constraint to the velocity field to achieve a spatial continuity of the velocity field, and further wherein the temporal minimization problem is defined to apply a temporal smoothing constraint and a periodic smoothing constraint to the velocity field to achieve a temporal continuity of the velocity field and prevent drifting artefacts in the Lagrangian coordinates.

10. The method of claim 1, wherein the Lagrangian coordinates computed for the biological body are identical whether the biological body is fixed or in motion.

11. A system for ultrasound imaging in presence of relative motion between a biological body and an imaging probe, the system comprising:

a processor; and a non-transitory computer-readable medium having stored thereon program code executable by the processor for:

obtaining a plurality of Eulerian-based ultrasound images of the biological body acquired with the imaging probe at successive times T during an entire cycle of natural movement of the biological body;

computing Lagrangian coordinates for the biological body using data from the Eulerian-based ultrasound images, the Lagrangian coordinates accounting for motion of the biological body over time during the entire cycle of natural movement of the biological body, wherein computing the Lagrangian coordinates for the biological body comprises:

determining Doppler velocities from the Eulerian-based ultrasound images, comprising regularizing the Doppler velocities in time and space by solving a spatial minimization problem and a temporal minimization problem; and converting the Doppler velocities into the Lagrangian coordinates;

forming, using a Lagrangian beamformer, Lagrangian-based ultrasound images of the biological body in the Lagrangian coordinates by providing the data from the Eulerian-based ultrasound images in the Lagrangian coordinate system, the Lagrangian beamformer configured to provide correction for the motion during the entire cycle of natural movement of the biological body; and filtering the Lagrangian-based ultrasound images to locate, throughout the entire cycle of natural movement of the biological body, positions of microbubbles injected into a blood stream.

12. The system of claim 11, wherein converting the Doppler velocities into the Lagrangian coordinates comprises:

setting the Lagrangian coordinates for a time T to Eulerian coordinates of the Eulerian-based ultrasound images; and estimating a displacement of the Eulerian coordinates from the time T to a time T+1 from the Doppler velocities.

13. The system of claim 12, wherein converting the Doppler velocities into the Lagrangian coordinates comprises setting the Lagrangian coordinates for the time T and estimating the displacement of the Eulerian coordinates from the time T to the time T+1 iteratively to regularize the Lagrangian coordinates.

14. The system of claim 11, wherein the biological body is a heart.

15. The system of claim 14, wherein the times T are synchronized with a cardiac cycle of the heart.

16. The system of claim 11, wherein filtering the Lagrangian-based ultrasound images to locate the positions of the microbubbles comprises:

applying a sliding window Singular Value Decomposition (SVD) filter to the Lagrangian-based ultrasound images to obtain SVD-filtered images; and correlating the SVD-filtered images to a simulated point spread function (PSF) to locate the positions of the microbubbles.

17. The system of claim 11, wherein the spatial minimization problem is defined to minimize a noise influence in a velocity field of the Doppler velocities and to apply a spatial smoothing constraint to the velocity field to achieve a spatial continuity of the velocity field, and further wherein the temporal minimization problem is defined to apply a temporal smoothing constraint and a periodic smoothing constraint to the velocity field to achieve a temporal continuity of the velocity field and prevent drifting artefacts in the Lagrangian coordinates.

18. The system of claim 11, wherein the Lagrangian coordinates computed for the biological body are identical whether the biological body is fixed or in motion.

19. The system of claim 11, wherein the relative motion is a periodic motion.

20. The system of claim 11, wherein the ultrasound imaging is performed for ultrasound localization microscopy.

*     *     *     *     *